United States Patent [19]

Belzer et al.

[11] Patent Number: 4,873,230

[45] Date of Patent: * Oct. 10, 1989

[54] COMPOSITION FOR THE PRESERVATION OF ORGANS

[75] Inventors: Folkert O. Belzer; James H. Southard, both of Madison, Wis.

[73] Assignee: Wisconsin Alumni Research Foundation, Madison, Wis.

[ * ] Notice: The portion of the term of this patent subsequent to Jan. 17, 2006 has been disclaimed.

[21] Appl. No.: 225,102

[22] Filed: Jul. 27, 1988

Related U.S. Application Data

[62] Division of Ser. No. 784,435, Oct. 3, 1985, Pat. No. 4,798,824.

[51] Int. Cl.$^4$ ............................................. A61K 31/715
[52] U.S. Cl. ...................................... 514/60; 514/832; 435/1; 435/283
[58] Field of Search .......................... 514/60, 3, 4, 832; 435/1, 283

[56] References Cited

U.S. PATENT DOCUMENTS 3,523,938  8/1970  Hershenson et al. ............... 536/111

FOREIGN PATENT DOCUMENTS 3030863  3/1982  Fed. Rep. of Germany ........ 514/60

Primary Examiner—John W. Rollins
Attorney, Agent, or Firm—Howard W. Bremer; Gildo E. Fato

[57] ABSTRACT

The present invention relates to new compositions for the preservation of organs prior to implantation comprising hydroxyethyl starch substantially free of ethylene glycol, ethylene chlorohydrin and acetone in a pharmaceutically acceptable organ perfusate.

2 Claims, 2 Drawing Sheets

COMPARISON OF HUMAN SERUM ALBUMIN (HSA) AND HYDROXYETHYL STARCH (HES) PERFUSATES ON RENAL FUNCTION AFTER 3 DAYS OF PERFUSION PRESERVATION.

EFFECTS OF DIALYSIS OF "HES" ON POST-TRANSPLANT RENAL FUNCTION AFTER 5 DAYS OF PRESERVATION.

EFFECT OF DIALYSIS OF "HES" ON POST-TRANSPLANT RENAL FUNCTION AFTER 7 DAYS OF PRESERVATION.

COMPOSITION FOR THE PRESERVATION OF ORGANS

This application is a division of application Ser. No. 784,435, filed 10/3/85, now U.S. Pat. No. 4,798,824.

BACKGROUND OF THE INVENTION

Renal preservtion, the ex vivo storage of cadaveric kidneys, is a relatively new field. Preservation of cadaveric kidneys for transplantation is common practice in hospitals; however, advances have been limited to trial and error experimentation. Although this approach has been partially successful from a clinical standpoint, the actual principles behind these successes are not well understood.

As renal transplantation has evolved from a strictly research procedure to an established clinical therapy for end-stage renal disease, renal preservation has progressed from the laboratory research stage to an established clinical method. At present, the two most commonly used methods for renal preservation are simple hypothermic storage and continuous perfusion. With simple hypothermic storage, the most common method of clinical renal preservation, the organs are removed from the cadaver donor and are cooled rapidly. This is usually achieved by a combination of external cooling and a short period of perfusion to drop the core temperature as quickly as possible. The kidneys are then stored, immersed in a flush-out solution in a simple plastic container, and kept at a temperature of 0° to 4° by immersing the container in ice. The advantages of this method are its simplicity, its low cost, and the ease of transportation of the organs. The composition of the flush-out solution to provide optimum preservation has been extensively studied.

The second method of renal preservation which has undergone extensive laboratory investigation, as well as clinical testing, is continuous pulsatile perfusion. The basic ingredients of continuous perfusion are (1) pulsatile flow, (2) hypothermia, (3) membrane oxygenation, and (4) a perfusate containing both albumin and lipids. With minor modifications, all presently used clinical preservation units share these basic principles. There are several advantages to continuous perfusion in clinical transplantation. First, perfusion provides enough time to make cadaveric transplantation a partly elective procedure. Second, it allows viability testing prior to implantation. A significant improvement in the results of cadaveric renal transplantation could be expected if the preservation time could be extended to the 5 to 7 days required for present methods of mixed lymphocyte culture testing.

The ability to successfully preserve human kidneys for two to three days by either simple cold storage after initial flushing with an intracellular electrolyte solution or by pulsatile perfusion with an electrolyte-protein solution has allowed sufficient time for histo-compatibility testing of the donor and recipient, kidney sharing among transplant centers, careful preoperative preparation of the recipient, time for preliminary donor culture results to become available, and vascular repairs of the kidney grant prior to implantation. Kidneys preserved for 72 hours using hypothermic pulsatile perfusion with cryoprecipitated plasma proved to be a significant advance for human kidney preservation and is currently the preferred method of preservation. Kidney organ preservation with ice-cold intracellular electrolyte flush solution followed by simple cold storage has been satisfactorily employed for human kidney preservation for up to 61 hours.

Serum albumin, in various forms, is used exclusively for clinical organ preservation to produce the necessary oncotic pressure. These forms include cryoprecipitated plasma, plasma protein fraction, human serum albumin, and silica gel-treated plasma. However, because these perfusates are prepared from naturally derived materials, variation is unavoidable. It would be particularly advantageous if a perfusate containing a synthetic colloid was available.

In the past, a large number of synthetic colloidal materials have been experimentally tested for effectiveness in kidney preservation. These colloids include dextrans, polyvinyl pyrrolidine, pluronics, hydroxyethyl starch (HES), Ficoll, gum arabic, and polyethylene glycol. None of these were as effective as serum albumin. However, HES was effective for 24 hours of preservation and in some cases for 72 hours of preservation. These colloidal materials were all tested in saline-based perfusates. Recently, excellent 72-hour preservation of canine kidney was observed with a perfusate containing gluconate anions in place of chloride with human serum albumin (HSA) for colloid osmotic support.

In accordance with the present invention a method of preserving kidneys using a perfusate containing HES in place of human serum albumin is disclosed.

As indicated hereinabove, serum albumin (HSA) based perfusates have been the standard for preservation of kidneys both experimentally and clinically for the past 17 years. Unfortunately preservation periods of only three days could be obtained with these types of perfusates. Although both of these methods preserve kidney viability for up to three days, longer preservation times are difficult to obtain consistently. Moreover, even though these methods preserve viability for up to three days, the kidneys are damaged as indicated by the elevated post-transplantation serum creatinine levels and time required to return those elevated levels to normal. Early perfusates were chosen from electrolyte solutions readily available for intravenous infusion and were basically of extracellular composition.

Heretofore, acceptable methods for renal preservation have not been available. Those that have been proven clinically effective are limited to short-term storage (three days) and significantly reduced viability. The present invention describes the biochemical composition of the perfusate best suited for the hypothermically perfused kidneys and a novel synthetic colloid osmotic agent that yields significantly improved long-term preservation.

DETAILED DESCRIPTION OF THE PREFERRED EMBODIMENT

Figure 1:
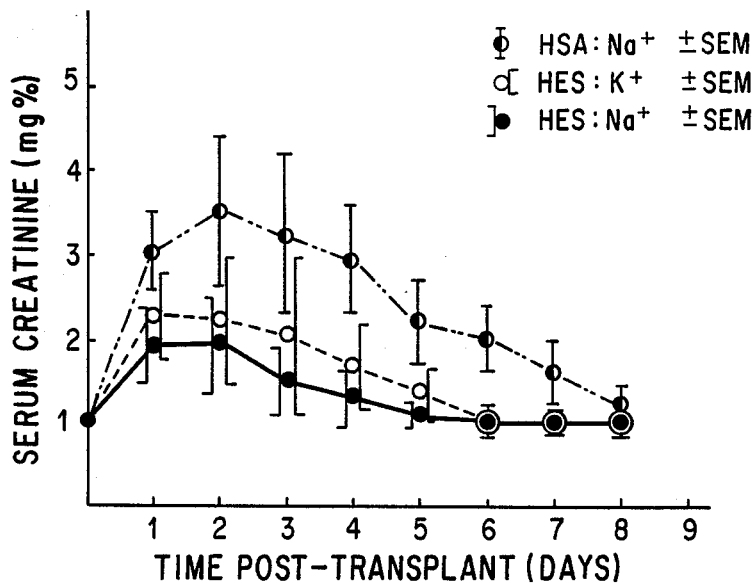
FIG. 1 is a comparison of human serum albumin and hydroxyethyl starch perfusates on renal function after three days of perfusion preservation in accordance with the prior art.

In accordance with the present invention the preferred colloid is hydroxyethyl starch having a weight average molecular weight of from about 150,000 to about 350,000 daltons and degree of substitution of from about 0.4 to about 0.7. A more preferred colloid is hydroxyethyl starch having a weight average molecular weight of from about 200,000 to about 300,000 daltons. In accordance with one embodiment of the present invention, the hydroxyethyl starch is dialyzed against distilled-deionized water or otherwise treated to remove several contaminants previously unknown to have an adverse affect on the effectiveness of hydroxyethyl starch preparations. The materials removed by the dialysis process are the very smallest hydroxyethyl starch components, including the ethylene glycol and ethylene chlorohydrin side products of the hydroxyethylation as well as the residual acetone and sodium chloride. Ethylene glycol and ethylene chlorohydrin are known to be toxic. Hence, their removal, even if present in small amount, is desirable.

In accordance with the present invention, the kidney perfusate composition includes, but is not limited to, the following:

Table 1

5% hydroxyethyl starch having a molecular weight of from about 200,000 to about 300,000 and a degree of substitution of from 0.4 to 0.7

25 mM $KH_2PO_4$
3 mM glutathione
5 mM adenosine
10 mM glucose
10 mM HEPES butter
5 mM magnesium gluconate
1.5 mM $CaCl_2$
105 mM sodium gluconate
200,000 units penicillin
40 units insulin
16 mg Dexamethasone
12 mg Phenol Red
pH 7.4–7.5

The post-transplant serum creatinine levels in dogs receiving a kidney preserved for three days with the hydroxyethyl starch (HES) perfusate is compared with the albumin (HSA) perfused kidney in FIG. 1 with HES as part of the perfusate, there is a slight elevation of the serum creatine during the first 2–4 days post-transplant followed by a rapid return to normal.

Figure 2:
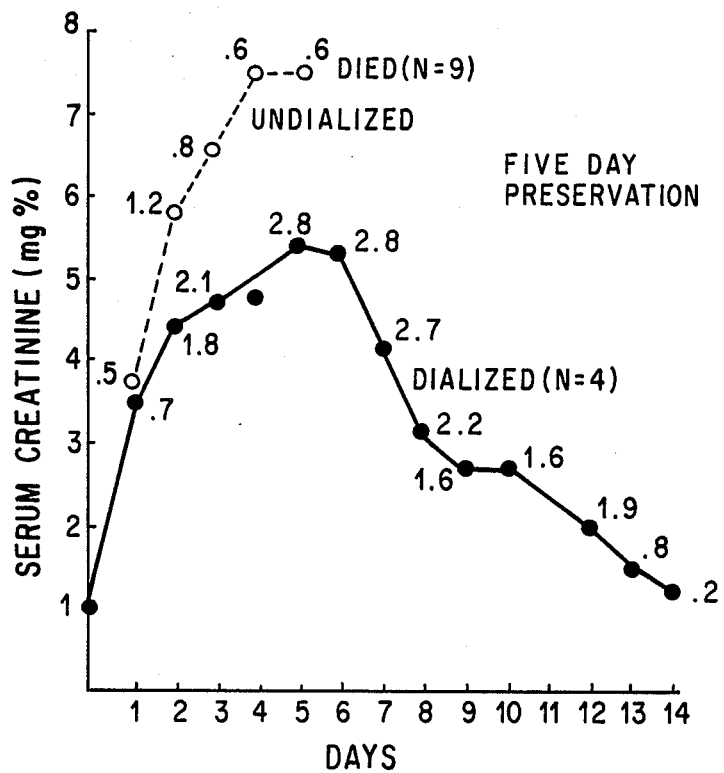
FIG. 2 shows the effects of dialysis of hydroxyethyl starch on post-transplant renal function after five days of perfusion preservation in accordance with the present invention, with the creatinine level indicated.

Extending the preservation time with this basic perfusate was unsuccessful until the starch was dialyzed prior to preparation of the perfusate. As shown in FIG. 2, the dialyzed starch gave successful preservation although the kidneys exhibited somewhat elevated serum creatinine values.

Figure 3:
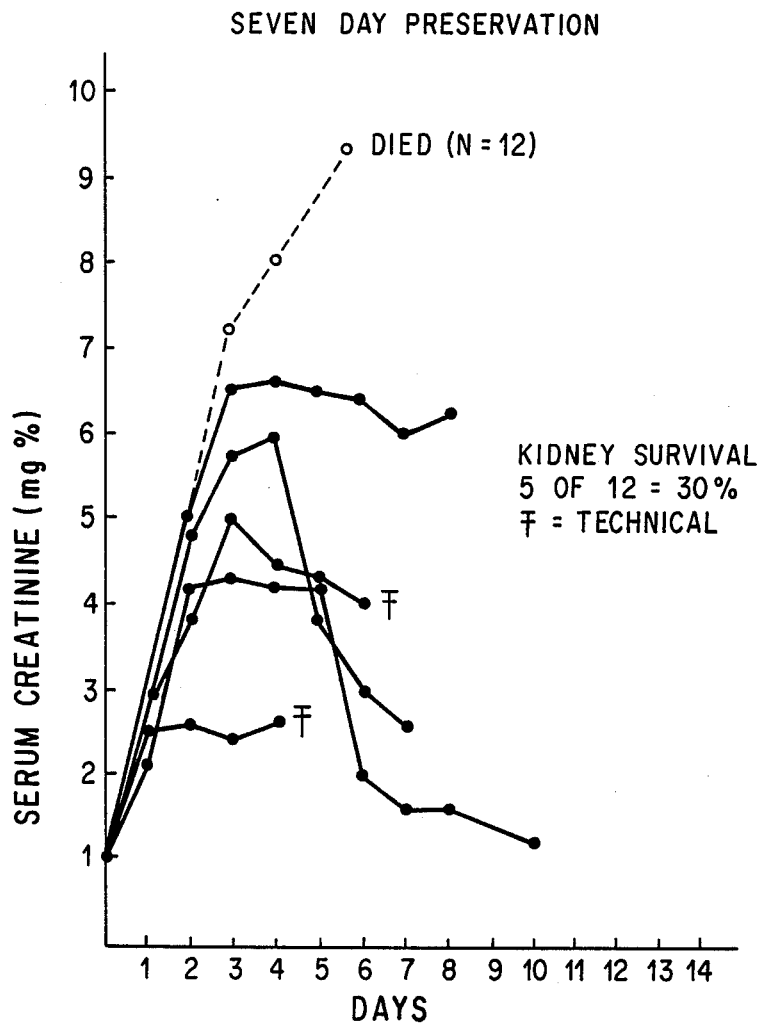
FIG. 3 shows the effects of dialysis of hydroxyethyl starch on post-transplant renal function after seven days of perfusion preservation in accordance with the present invention.

Seven day preservation of kidneys was accomplished with the HES-based perfusate. As shown in FIG. 3, five of 17 dogs (30%) survived seven day preservation. In all 17 dogs, none showed signs of endothelial damage. Thus, the HES-based perfusate extends the preservation time beyond that which was possible with the HSA perfusate.

In addition to the HES, the perfusate is radically different from other commonly used perfusates. Chloride has been replaced with the larger molecular weight (and less permeable) gluconate to suppress hypothermic induced cell swelling. Adenosine and $PO_4$ are included to stimulate ATP syntheses. Glutathion is added to suppress the loss of glutathione from perfused organs and to act as an antioxidant. The $K^+$ concentration is elevated to 25 mM to suppress the loss of intracellular $K^+$ at hypothermia and $PO_4$ and HEPES are used as buffers. The role of some of these agents have been shown to be beneficial to kidneys during preservation.

EXAMPLE 1

One hundred grams of hydroxyethyl starch was dissolved in one liter of distilled-deionized water to make a 10% w/w solution. The HES solution was placed in dialysis bags (34 mm×18 inches) having a molecular weight cut-off of 50,000 daltons, placed in a 10–15 liter container of distilled-deionized water, and stirred for 72 hours. The water was changed daily, and the HES was collected and frozen at $-20°$ C. until used.

EXAMPLE 2

Adult mongrel dogs (15 to 25 kg) were used in all cases. Surgical procedures and hypothermic pulsatile perfusion preservation were performed by conventional procedures. The composition of the perfusate is shown in Table 1. Kidneys were transplanted after 72 hours of preservation followed by immediate contralateral nephrectomy. Serum creatinine level was determined daily after the transplant.

Accordingly, the present invention provides extended clinical organ preservation time and, as a synthetic colloid, minimizes the variation which results from perfusates prepared from naturally derived materials.

The present invention has been described in detail and with particular reference to the preferred embodiments; however, it will be understood by one having ordinary skill in the art that changes can be made thereto without departing from the spirit and scope thereof.

We claim:

1. A composition of matter for the preservation of organs comprising hydroxyethyl starch having a molecular weight of from about 150,000 to about 350,000 daltons, degree of substitution of from about 0.4 to about 0.7, and being substantially free of ethylene glycol, ethylene chlorohydrin, sodium chloride and acetone.

2. The composition of matter of claim 1 wherein the hydroxyethyl starch has a molecular weight of from about 200,000 to about 300,000 daltons.

* * * * *

UNITED STATES PATENT AND TRADEMARK OFFICE
CERTIFICATE OF CORRECTION

PATENT NO. : 4,873,230

DATED : October 10, 1989

INVENTOR(S) : Folkert O. Belzer, et. al.

It is certified that error appears in the above-identified patent and that said Letters Patent is hereby corrected as shown below:

Column 1, line 4, insert the following:

"This invention was made with United States Government support awarded by the National Institutes of Health (NIH), Grant numbers: AM 18624 and DK 18624. The United States Government has certain rights in this invention.

Signed and Sealed this

Thirtieth Day of November, 1993

Attest:

BRUCE LEHMAN

Attesting Officer

Commissioner of Patents and Trademarks